United States Patent [19]

Ribaldone et al.

[11] 4,062,860
[45] Dec. 13, 1977

[54] PROCESS FOR PREPARING 3,4-DICYANO-1,2,5-THIADIAZOLE

[75] Inventors: Giuseppe Ribaldone, Gallarate (Varese); Renato Grecu, Cameri (Novara), both of Italy

[73] Assignee: Montedison S.p.A., Milan, Italy

[21] Appl. No.: 733,940

[22] Filed: Oct. 19, 1976

[30] Foreign Application Priority Data

Nov. 18, 1975 Italy .................................. 29384/75

[51] Int. Cl.$^2$ .......................................... C07D 285/10
[52] U.S. Cl. ............................................... 260/302 D
[58] Field of Search ................................... 260/302 D

[56] References Cited

PUBLICATIONS

Shew, *Ph D Dissertation*, 1959, Indiana University, pp. 11-13, 16 & 62.

*Primary Examiner*—Richard J. Gallagher
*Attorney, Agent, or Firm*—Hubbell, Cohen, Stiefel & Gross

[57] ABSTRACT 3,4-dicyano-1,2,5-thiadiazole is prepared by reacting diaminomaleonitrile (DAMN) with thionyl chloride ($SOCl_2$) at a temperature of 40° C. up to the boiling point of thionyl chloride wherein the molar ratio of $SOCl_2$/DAMN is between 2:1 and 10:1.

8 Claims, No Drawings

PROCESS FOR PREPARING 3,4-DICYANO-1,2,5-THIADIAZOLE

BACKGROUND OF THE INVENTION

1. Field of the Invention

The present invention relates to processes for preparing 3,4-dicyano-1,2,5-thiadiazole. In particular the present invention relates to processes for preparing 3,4-dicyano-1,2,5-thiadiazole which has the formula:

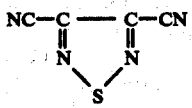 (I)

starting from diaminomaleonitrile (DAMN), which is a tetramer of hydrocyanic acid, a known commercially available intermediate for organic syntheses.

2. The Prior Art 3,4-dicyano-1,2,5-thiadiazole (I) is a known compound having known uses as intermediate for organic syntheses in general (polyamides, pigments, adhesives), besides being itself useful as a fungicide and bactericide.

Moreover, 3,4-dicyano-1,2,5-thiadiazole (I) can be used to obtain 1,2,5-thiadiazol-3,4-dicarboxylic acid, which is a starting material (monomeric compound) for the preparation of polyamide polymers used in forming efficient membranes for reverse osmosis. The technology based on the use of said membranes for reverse osmosis is of particular interest, for example, in desalting waters.

The known methods of preparing 3,4-dicyano-1,2,5-thiadiazole are based on (1) destructive oxidation of 4-nitro-2,1,3-benzothiazole with $KMnO_4$, the former being obtained from 3-nitrophenylenediamine and $S_2Cl_2$, or (2) by reaction of hydrocyanic acid, chlorine and $SCl_2$ or sulphur in a solvent (chlorinated) in the presence of trimethylamine.

These methods are of little use for commercial scale operations because of the low yields and complicated separation and purification operations required.

In fact, the destructive oxidation methods involve particularly large amounts of impurities, while the preparation starting from HCN, chlorine and $SCl_2$ or sulphur is complicated by the presence of solvents and catalysts (for example trimethylamine) which must be removed and recovered.

It is an object of this invention to provide processes for preparing 3,4-dicyano-1,2,5-thiadiazole in a simple and economical way, without the disadvantages of the known methods.

Another object is to provide processes for preparing 1,2,5-thiadiazole-3,4-dicarboxylic acid that are practicable on a commercial scale.

SUMMARY OF THE INVENTION

The present invention provides processes for preparing 3,4-dicyano-1,2,5-thiadiazole (I) comprising reacting diaminomaleonitrile (DAMN) with thionyl chloride, wherein the $SOCl_2$/DAMN molar ratio is between 2:1 and 10:1, at a temperature ranging from 40° to the boiling point of $SOCl_2$. The reaction on which the process of the present invention is predicated is represented by the following equation (1):

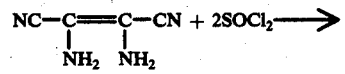
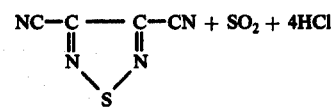 (1)

The invention may therefore be more clearly defined as a process in which a heterogeneous mixture, consisting of diaminomaleonitrile (a solid) and thionyl chloride (a liquid) at a $SOCl_2$/DAMN molar ratio at least equal to 2:1 and not exceeding 10:1, is reacted at a temperature ranging from 40° to 79° C. (boiling point of $SOCl_2$) until complete evolution of the reaction gases has occured. The reaction is followed, according to substantially conventional techniques, by separating the excess, if any, of thionyl chloride, by distillation after which the 3,4-dicyano-1,2,5-thiadiazole (I) is isolated by vacuum distillation or extraction with solvents, such as ethyl ether, methylene chloride, chloroform, etc.

In the case where the 3,4-dicyano-1,2,5-thiadiazole, is to be employed as an intermediate for preparing 1,2,5-thiadiazol-3,4-dicarboxylic acid, the crude reaction product containing the 3,4-dicyano-1,2,5-thiadiazole may be utilized directly without effecting any prior separation thereof.

In fact, the monopotassium salt of 1,2,5-thiadiazol-3,4-dicarboxylic acid can easily be obtained from the reaction mass containing 3,4-dicyano-1,2,5-thiadiazole, without isolating the latter, by means of saponification with aqueous KOH and subsequent acidification with aqueous HCl, according to reactions (2) and (3):

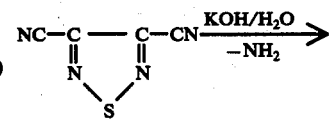
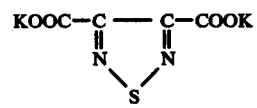 (2)

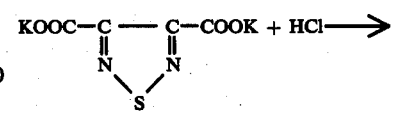
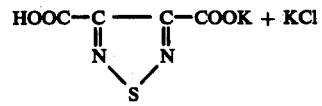 (3)

The monopotassium salt is the intermediate used for the preparation of the above-mentioned reverse osmosis membranes. Both the ratio of thionyl chloride to DAMN and the reaction temperature must be within the indicated ranges which are critical parameters for the correct conduct of the reaction.

As is clearly seen from equation (1), in order to form 3,4-dicyano-1,2,5-thiadiazole, at least two moles of $SOCl_2$ are required per 1 mole of DAMN. The reaction stoichiometry, which is not heretofore known, will be confirmed below.

While the SOCl$_2$/DAMN molar ratio, as noted above, must be between 2:1 and 10:1, it is preferred to use a ratio of from 3:1 to 5:1.

Such amounts of SOCl$_2$, besides assuring a practically complete conversion of DAMN, render the stirring of the reagent mass easier, particularly at the beginning of the heterogeneous reaction. On the other hand, as will be experimentally shown below, SOCl$_2$/DAMN molar ratios higher than 10:1 are of no practical use, because they require larger volumes of reagents, larger amounts of SOCl$_2$ to be recovered and recycled, etc. Moreover, such higher ratios (e.g., higher than 10:1), in fact have proven to be detrimental to the course of the reaction itself, because they invariably lead to an incomplete conversion of DAMN and to lower total yields.

The preferred reaction temperatures ranges from 40° to about 75° C. and in practice it is possible to come very close to the boiling point of SOCl$_2$ (79° C.) at atmospheric pressure, without actually reaching it, in order to prevent the reagent mixture from boiling. In fact, at a temperature from 45° to 75° C., the course of the reaction is quite regular without any diminution in the reaction rate.

Conversely, when the reaction is conducted at the SOCl$_2$ boiling point (79° C.), no practical advantage is attained as regards the heat consumption, although higher losses of SOCl$_2$ may occur through the cooling system and also due to the entraining action of the evolving reaction gases.

In fact, in such cases, an impoverishment of SOCl$_2$ of the reaction mixture may occur.

As a result, the reaction is preferably conducted isothermally at temperatures in the range of from 40° to 75° C.

According to an effective alternative procedure, the reaction can be conducted in two temperature steps, a first step which is between 45° and 60° C., and a second step, in which it is raised to between 60° and 75° C. By using this alternative, the course of the reaction can be controlled more exactly and more easily.

In general, reaction times of between 1.5 and 10 hours, depending on the molar ratio and the temperature employed, are sufficient to complete the reaction.

In more detail, a practical embodiment of the process according to the invention can be carried out as follows: a mixture of diaminomaleonitrile and thionyl chloride in a SOCl$_2$/DAMN molar ratio of 3-5 is first prepared. Then the temperature is adjusted to 45°-60° C. whereupon the evolution of gas begins at once. As soon as the gas evolution, which in this first step is very remarkable, tends to slow down, the temperature is raised to 60°-75° C., and is maintained thereat until the gas evolution stops.

The reacting mixture, which is at first heterogeneous, becomes more and more fluid as the reaction proceeds, until it finally becomes a homogeneous liquid.

The reaction mixture is then distilled under atmospheric pressure in order to remove the excess, if any, thionyl chloride, and then under vacuum at 1–2 mm Hg to recover the 3,4-dicyano-1,2,5-thiadiazole. Upon cooling, the distilled 3,4-dicyano-1,2,5-thiadiazole solidifies, providing a practically pure product.

Alternatively, it is possible to isolate the 3,4-dicyano-1,2,5-thiadiazole according to the following method: the reacted mixture, after distillation of the excess (if any) thionyl chloride, is extracted with a solvent such as ethyl ether, methylene chloride or chloroform. The thus obtained extract is washed with water and evaporated to a small volume. The 3,4-dicyano-1,2,5-thiadiazole crystallizes upon cooling or by the addition of petroleum ether.

If it is desired to convert the 3,4-dicyano-1,2,5-thiadiazole into the monopotassium salt of 1,2,5-thiadiazol-3,4-dicarboxylic acid, the reaction mixture, after removal by distillation of the excess thionyl chloride, is directly treated with aqueous KOH until the evolution of ammonia ceases. After acidification to a pH of about 2.5, the monopotassium salt of 1,2,5-thiadiazol-3,4-dicarboxylic acid which is sparingly water-soluble precipitates out. The resulting salt is sufficiently pure for the intended uses.

This present process is particularly advantageous because of the mild and simple operating conditions.

A particular advantage of the process is the high yield and the high purity attainable for the product.

An additional advantage, of course, is the possibility of directly employing the reaction product, without any preliminary purification, as in the case of the use of the obtained 3,4-dicyano-1,2,5-thiadiazole for preparing 1,2,5-thiadiazol-3,4-dicarboxylic acid.

DESCRIPTION OF THE PREFERRED EMBODIMENTS

The present invention will now be further described in the following examples, which are not to be considered limitative, but rather as merely illustrative of the invention which is defined in the claims. In these examples, Example 1 is given to prove the stoichiometry of the reaction, Example 2 is given to demonstrate the preparation of the monopotassium salt of 1,2,5-thiadiazol-3,4-dicarboxylic acid and, finally, Example 4 is given to prove that the values given for the SOCl$_2$/DAMN molar ratio are critical.

EXAMPLE 1

10.8 g. of diaminomaleonitrile and 35.7 g. of thionyl chloride (SOCl$_2$/DAMN molar ratio = 3) were introduced into a cylindrical reactor equipped with a heating jacket, thermometer, stirrer, reflux cooler and at the upper end of the reactor, a valve for controlling the evolution of the gas.

The mixture was heated with stirring to 50° C. for 1.5 hours: a gas consisting of HCl and SO$_2$ evolved, at first very intensely, and then gradually, at a slower rate. Then the mixture was heated to 75° C. for 1.5 hours, during which step the heterogeneous mixture of reagents became more and more fluid until finally turning into a liquid. At the end of the 1.5 hour time-period the evolution of gases had completely stopped. The reflux cooler was then replaced by a distillation head and the excess thionyl chloride was distilled off at atmospheric pressure. The residue, consisting of raw 3,4-dicyano-1,2,5-thiadiazole, was then distilled under vacuum at 1-2 mm Hg, and the distillate was collected at 75°-80° C. During the distillation, both the distillation head and condenser were thermoregulated at 65° C. to prevent the distillate from solidifying.

There were obtained 11.97 g. of 3,4-dicyano-1,2,5-thiadiazole as a liquid product, which upon cooling, yielded a solid mass having a melting point = 50°-50.5° C.

The yield, based on diaminomaleonitrile, was 88%. The infrared spectrum of the thus obtained product was thoroughly identical with that of an authentic sample of 3,4-dicyano-1,2,5-thiadiazole.

An analysis of the reaction gases, which were absorbed in a 10% NaOH solution during the course of the reaction, provided the following molar ratio:

$HCl : SO_2 : DAMN = 4.08 : 1.01 : 1$ which is in full agreement with the stoichiometry of equation (1).

EXAMPLE 2

10.8 g. of diaminomaleonitrile and 35.7 g. of thionyl chloride ($SOCl_2$/DAMN molar ratio = 3) were introduced into the equipment described in Example 1. The mixture was heated with stirring at 75° C. After about 2 hours at this temperature, the mixture of reagents had become completely liquid, without any further evolution of gas. The reflux cooler was replaced by a distillation head the the excess thionyl chloride was distilled off at atmospheric pressure.

The distillation residue, consisting of 3,4-dicyano-1,2,5-thiadiazole, was gradually admixed with a solution of 14.2 g. of 85% KOH in 36 g. of $H_2O$, after which it was heated to 90° C. for 2 hours.

After this 2 hour time-period, the evolution of $NH_3$ had completely stopped. The resulting solution, containing the dipotassium salt of 1,2,5-thiadiazol-3,4-dicarboxylic acid, was cooled to room temperature and acidified with stirring to a pH of 2.5 with concentrated hydrochloric acid.

The resulting yellow precipitate was filtered and dried to constant weight. In this way there were obtained 21.7 g. of the monopotassium salt of 1,2,5-thiadiazol-3,4-dicarboxylic acid, having a titer of 89%, the impurity consisting of potassium chloride.

The monopotassium salt yield, based on diaminomaleonitrile was 91%. A sample of the product crystallized again from water had a melting point of 293° C. (with decomposition) and an infrared spectrum quite identical with that of an authentic sample of monopotassium salt of 1,2,5-thiadiazol-3,4-dicarboxylic acid.

EXAMPLE 3

10.8 g. of diaminomaleonitrile and 59.5 g. of thionyl chloride ($SOCl_2$/DAMN molar ratio = 5) were introduced into the equipment described in Example 1.

The resulting mixture was heated to 70° C. for 2 hours, after which the reflux cooler was replaced by a distillation head and the excess thionyl chloride was distilled off at atmospheric pressure. The distillation residue, consisting of 3,4-dicyano-1,2,5-thiadiazole was then dissolved in ethyl ether. The ether solution was washed with water, dried over sodium sulphate and concentrated to a small volume. 3,4-dicyano-1,2,5-thiadiazole was crystallized by the addition of petroleum ether, and then filtered and dried. 9.0 g. of product were obtained, having chemical and physical characteristics identical with those of the product obtained in Example 1.

EXAMPLE 4

In the equipment described in Example 1, a series of systematic tests was carried out employing various $SOCl_2$/DAMN molar ratios, in order to establish what amount of $SOCl_2$ allows a complete conversion of DAMN. All the tests were conducted while keeping the reacting mixture under boiling (79° C.), in order to attain the maximum reaction rate.

Tests to determine the completion of the reaction were effected by analyzing the reaction mixture at different times by means of chromatography on a thin silica gel layer.

The obtained results are reported in the following table.

TABLE

| $SOCl_2$-DAMN molar ratio | DAMN Conversion | | | |
|---|---|---|---|---|
| | 1 hr. | 2.5 hr. | 5 hr. | 7 hr. |
| 50 | incomplete | incomplete | incomplete | incomplete |
| 30 | " | " | " | " |
| 20 | " | " | " | " |
| 15 | " | " | " | " |
| 10 | " | " | complete | — |

From the data in this table it is clearly seen that the conversion of DAMN is never completed when the $SOCl_2$/DAMN molar ratio is higher than 10.

Variations and modifications can, of course, be made without departing from the spirit and scope of the invention.

What we desire to secure by Letters Patent and hereby claim is:

1. A process for preparing 3,4-dicyano-1,2,5-thiadiazole comprising reacting diaminomaleonitrile with thionyl chloride wherein the thionyl chloride/diaminomaleonitrile molar ratio is from 2:1 to 10:1 at a temperature between 40° C. and the boiling point of thionyl chloride.

2. A process according to claim 1, wherein th thionyl chloride/diaminomaleonitrile molar ratio is between 3:1 and 5:1.

3. A process according to claim 1, wherein the temperature is 45° to 75° C.

4. A process according to claim 2, wherein the temperature is 45° to 75° C.

5. A process according to claim 1, wherein the reaction is conducted in two steps, a first step at a temperature of 45°–60° C. and a second step at a temperature of 60°–75° C.

6. A process according to claim 2, wherein the reaction is conducted in two steps, a first step at a temperature of 45°–60° C. and a second step at a temperature of 60°–75° C.

7. A process according to claim 3, wherein the reaction is conducted in two steps, a first step at a temperature of 45°–60° C. and a second step at a temperature of 60°–75° C.

8. A process according to claim 1, and further comprising treating the 3,4-dicyano-1,2,5-thiadiazole with aqueous KOH to form the dipotassium salt of 1,2,5-thiadiazol-3,4-dicarboxylic acid and acidifying same with aqueous HCl to form the monopotassium salt thereof.

* * * * *

UNITED STATES PATENT OFFICE
CERTIFICATE OF CORRECTION

Patent No. 4,062,860                    Dated December 13, 1977

Inventor(s) Giuseppe Ribaldone et al

It is certified that error appears in the above-identified patent and that said Letters Patent are hereby corrected as shown below:

Column 3, line 16: "temperatures" should read -- temperature --.

Column 6, Table, in the heading: "$SOCl_2 1-$" should read -- $SOCl_2/-$ --.

Column 6, line 1 of claim 2: "th" should read -- the --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks